(12) United States Patent
Tanimura et al.

(10) Patent No.: US 11,510,610 B2
(45) Date of Patent: Nov. 29, 2022

(54) EATING MONITORING METHOD, PROGRAM, AND EATING MONITORING DEVICE

(71) Applicant: SHARP KABUSHIKI KAISHA, Sakai (JP)

(72) Inventors: Motoki Tanimura, Sakai (JP); Daisuke Kamata, Sakai (JP); Hiroki Terabe, Sakai (JP)

(73) Assignee: SHARP KABUSHIKI KAISHA, Sakai (JP)

(*) Notice: Subject to any disclaimer, the term of this patent is extended or adjusted under 35 U.S.C. 154(b) by 424 days.

(21) Appl. No.: 16/558,944

(22) Filed: Sep. 3, 2019

(65) Prior Publication Data

US 2020/0113512 A1 Apr. 16, 2020

(30) Foreign Application Priority Data

Oct. 10, 2018 (JP) .............................. JP2018-191869

(51) Int. Cl.
*A61B 5/00* (2006.01)
*A61B 5/11* (2006.01)
*G06F 17/18* (2006.01)
*G06V 40/20* (2022.01)

(52) U.S. Cl.
CPC .......... *A61B 5/4542* (2013.01); *A61B 5/1126* (2013.01); *A61B 5/6815* (2013.01); *A61B 5/7225* (2013.01); *G06F 17/18* (2013.01); *G06V 40/20* (2022.01); *A61B 2562/0219* (2013.01)

(58) Field of Classification Search
None
See application file for complete search history.

(56) References Cited

U.S. PATENT DOCUMENTS 6,893,406 B2* 5/2005 Takeuchi ............. A61B 5/0088
600/590
2006/0064037 A1* 3/2006 Shalon .................. G16H 20/60
600/586

(Continued)

FOREIGN PATENT DOCUMENTS

JP 2005-349176 A 12/2005
JP 2012-120832 A 6/2012

(Continued)

*Primary Examiner* — Charles A Marmor II
*Assistant Examiner* — Benjamin S Melhus
(74) *Attorney, Agent, or Firm* — ScienBiziP, P.C.

(57) ABSTRACT

The present invention provides an eating monitoring method for judging whether chewing is performed or not by a chewing judgment algorithm on the basis of a temporal variation in a measured value of a sensor unit configured to detect a movement of a jaw while a person takes a meal, the person wearing a detection device comprising the sensor unit. The method includes the steps of: adjusting the chewing judgment algorithm on the basis of a variation in a measured value of the sensor unit, the variation corresponding to a chewing action or a mouth opening/closing action of the person wearing the detection device; and judging whether chewing is performed or not by the chewing judgment algorithm which has been adjusted, and measuring the number of chews on the basis of a temporal variation in a measured value of the sensor unit during the meal.

14 Claims, 8 Drawing Sheets

(56) References Cited

U.S. PATENT DOCUMENTS

| | | | |
|---|---|---|---|
| 2014/0251023 A1* | 9/2014 | Magomedov | A61B 5/11 73/779 |
| 2017/0042468 A1 | 2/2017 | Tanimura et al. | |
| 2017/0049361 A1 | 2/2017 | Tanimura et al. | |
| 2018/0242908 A1* | 8/2018 | Sazonov | A61B 5/7278 |
| 2020/0337635 A1* | 10/2020 | Sazonov | A61B 5/4542 |

FOREIGN PATENT DOCUMENTS

| | | |
|---|---|---|
| JP | 2015-208634 A | 11/2015 |
| JP | 2016-140478 A | 8/2016 |
| JP | 2018-033568 A | 3/2018 |
| WO | 2015/166739 A1 | 11/2015 |
| WO | 2015/166740 A1 | 11/2015 |
| WO | 2016/117477 A1 | 7/2016 |
| WO | 2018/042702 A1 | 3/2018 |

* cited by examiner

EATING MONITORING METHOD, PROGRAM, AND EATING MONITORING DEVICE

CROSS-REFERENCE TO RELATED APPLICATION

This application is related to Japanese Patent Application No. 2018-191869 filed on Oct. 10, 2018, whose priority is claimed under 35 USC § 119, and the disclosure of which is incorporated by reference in its entirety.

BACKGROUND OF THE INVENTION

1. Field of the Invention

The present invention relates to an eating monitoring method, a program, and an eating monitoring device.

2. Description of the Background Art

Wearable sensors have received attention from the viewpoint of lifestyle modification, early detection of diseases, and physical condition management.

For example, a wearable sensor capable of measuring the number of chews has been known (for example, JP 2015-208634 A, JP 2016-140478 A, and WO 2018/042702 A1). The sensor described above measures the number of chews by detecting the movement of a jaw through measurement of the distance between the sensor and the jaw using a distance sensor.

When the number of chews during meal is small, obesity or indigestion may be caused. In view of this, the number of chews is numerically expressed by the wearable sensor, whereby a user can easily check the number of chews, and will be able to eat with the sufficient number of chews. In addition, the number of chews can be managed, which can be used for health control.

A conventional measuring device that measures the number of chews judges whether chewing is performed on the basis of a variation in a measured value of a sensor using a standard judgment algorithm. However, since human body information is sensed, the magnitude of the movement during chewing and the shape of a face differ for each user. Thus, the accuracy in judgment of chewing may be high for some people, and low for other people. That is, a variation in accuracy of the judgment of chewing may be caused due to personal differences.

SUMMARY OF THE INVENTION

The present invention is accomplished in view of the above circumstances, and aims to provide an eating monitoring method with which it is possible to reduce a variation in accuracy of judgment of chewing due to personal differences.

The present invention provides an eating monitoring method for judging whether chewing is performed using a chewing judgment algorithm on the basis of a temporal variation in a measured value of a sensor unit, when a person wearing a detection device takes a meal, the sensor unit being provided to the detection device for detecting a movement of a jaw, the method comprising: a step for adjusting the chewing judgment algorithm on the basis of a variation in a measured value of the sensor unit corresponding to a chewing action or a mouth opening/closing action of the person wearing the detection device; and a step for judging whether chewing is performed on the basis of a temporal variation in a measured value of the sensor unit during a meal using the chewing judgment algorithm which has been adjusted, and measuring the number of chews.

In the eating monitoring method according to the present invention, the chewing judgment algorithm adjusted for each user is used, whereby a variation in accuracy of judgment of chewing caused by personal differences can be reduced.

DESCRIPTION OF THE PREFERRED EMBODIMENTS

Figure 1:
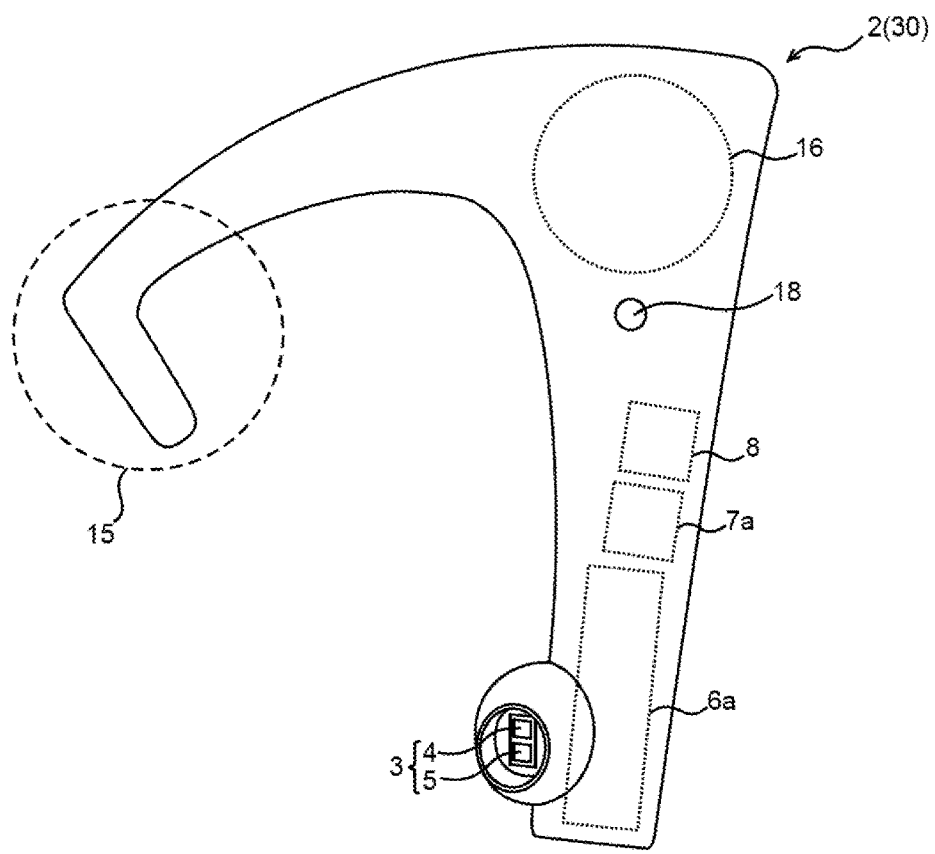
FIG. 1 is a schematic perspective view of a detection device included in an eating monitoring device according to one embodiment of the present invention.

The eating monitoring method according to the present invention is an eating monitoring method for judging whether chewing is performed using a chewing judgment algorithm on the basis of a temporal variation in a measured value of a sensor unit when a person wearing a detection device takes a meal, the sensor unit being provided to the detection device for detecting a movement of a jaw, the method comprising: a step for adjusting the chewing judgment algorithm on the basis of a variation in a measured value of the sensor unit corresponding to a chewing action or a mouth opening/closing action of the person wearing the detection device; and a step for judging whether chewing is performed on the basis of a temporal variation in a measured value of the sensor unit during a meal using the chewing judgment algorithm which has been adjusted, and measuring the number of chews.

In the eating monitoring method according to the present invention, it is preferable that, in the step for adjusting the chewing judgment algorithm, the chewing judgment algorithm is adjusted for each of a chewing action on the right side and a chewing action on the left side of the person wearing the detection device. With this configuration, the chewing action on the right side and the chewing action on the left side of a user during the meal can be detected. Further, the user may be notified of the number of chews on the right side and the number of chews on the left side, which may lead to elimination of the habit of chewing on preference side (chewing laterality).

It is preferable that the eating monitoring method according to the present invention further comprises a step for comparing a variation in the measured value of the sensor unit corresponding to the mouth opening/closing action of the person wearing the detection device with statistical data. With this configuration, a possibility of diseases such as temporomandibular arthrosis can be found.

It is preferable that the detection device is provided with an acceleration sensor, and the eating monitoring method according to the present invention further comprises a step for adjusting a posture judgment algorithm on the basis of a measured value of the acceleration sensor corresponding to a posture of a person wearing the detection device, and a step for judging a posture of the person wearing the detection device during a meal on the basis of the measured value of the acceleration sensor using the adjusted posture judgment algorithm. With this configuration, a change in the posture of the user during the meal can be detected, and the measured value of the sensor unit can be corrected. Thus, the accuracy in the judgment of chewing can be improved.

The present invention also provides a program that causes a computer to execute the eating monitoring method according to the present invention.

The present invention also provides an eating monitoring device including the detection device and an information device provided so as to be communicable with the detection device, wherein the information device has a first control unit, and the first control unit is configured to execute the eating monitoring method according to the present invention.

The present invention also provides an eating monitoring device including the detection device, wherein the detection device has a second control unit, and the second control unit is configured to execute the eating monitoring method according to the present invention.

It is preferable that the detection device included in the eating monitoring device is formed into an L shape having a hook part on one end and the sensor unit on the other end, and has a battery placed at a corner of the L shape.

The present invention will be described below in more detail with reference to several embodiments. The configurations shown in the drawings and the following description are merely illustrative, and the scope of the present invention is not limited to those shown in the drawings and following description.

First Embodiment

Figure 2:
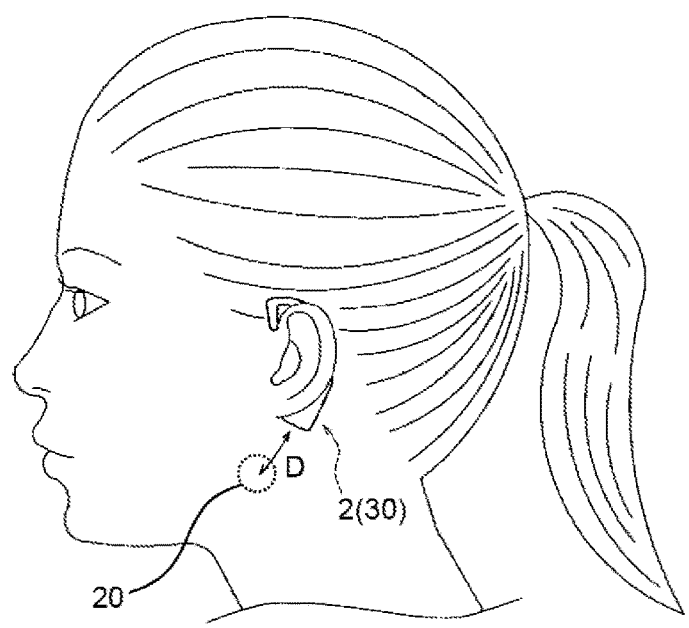
FIG. 2 is a schematic view showing a state in which the detection device included in the eating monitoring device according to one embodiment of the present invention is worn.
Figure 3A:
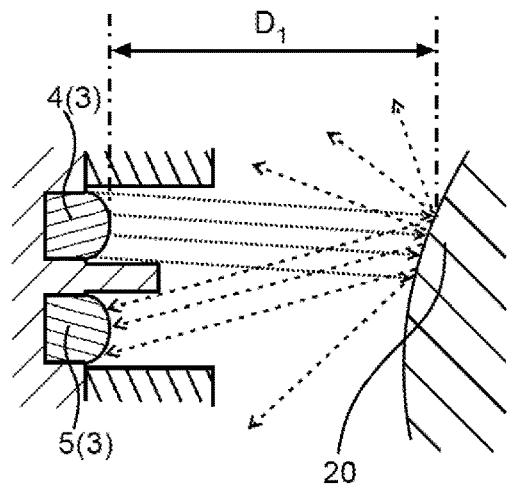
FIGS. 3A and 3B are explanatory views of optical path when the movement of a jaw is detected using a sensor unit.
Figure 3B:
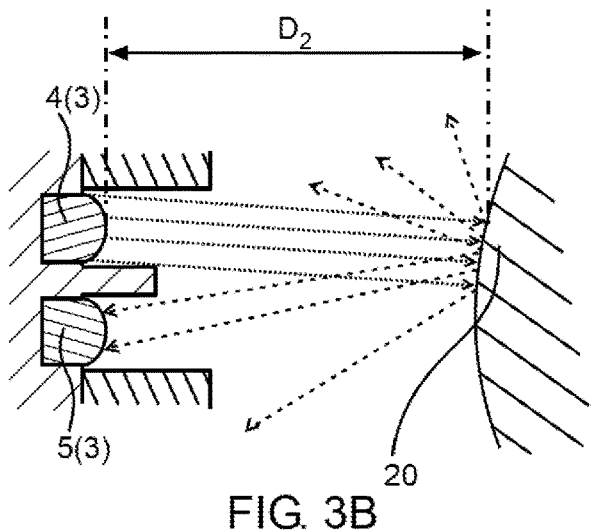
Figure 4:
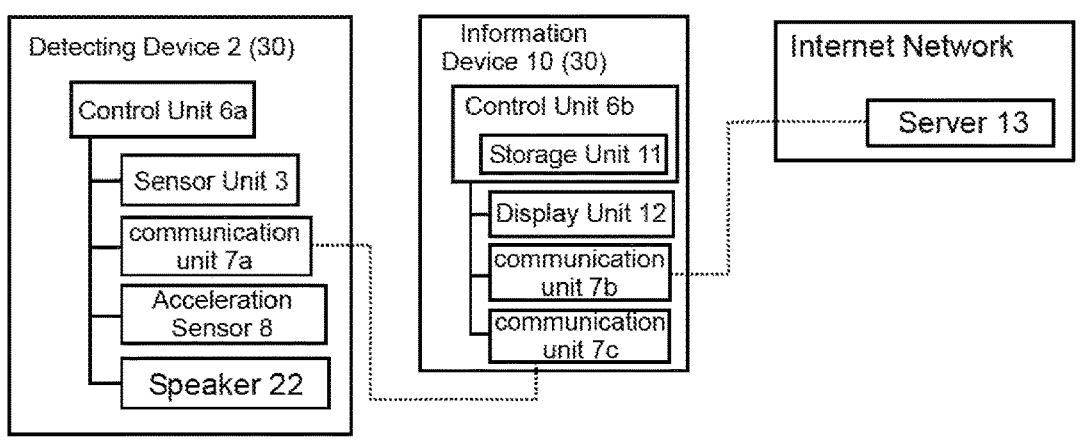
FIG. 4 is a block diagram showing the configuration of the eating monitoring device according to one embodiment of the present invention.

FIG. 1 is a schematic perspective view of a detection device included in an eating monitoring device according to the present embodiment, and FIG. 2 is a schematic view showing a state in which the detection device is worn. FIGS. 3A and 3B are explanatory views of an optical path when the movement of a jaw is detected using a sensor unit, and FIG. 4 is a block diagram of the eating monitoring device.

The eating monitoring method according to the present embodiment is an eating monitoring method for judging whether chewing is performed using a chewing judgment algorithm on the basis of a temporal variation in a measured value of a sensor unit 3 when a person wearing a detection device 2 takes a meal, the sensor unit 3 being provided to the detection device 2 for detecting a movement of the jaw. The eating monitoring method according to the present embodiment includes: a step for adjusting the chewing judgment algorithm on the basis of a variation in a measured value of the sensor unit 3 corresponding to a chewing action or a mouth opening/closing action of the person wearing the detection device 2; and a step for judging whether chewing is performed on the basis of a temporal variation in a measured value of the sensor unit 3 during a meal using the chewing judgment algorithm which has been adjusted, and measuring the number of chews.

The program according to the present embodiment is created to cause a computer to execute the eating monitoring method according to the present embodiment. The computer may be a microcontroller, a smartphone, a personal computer, a mobile computer, a smart watch, or a mobile phone, for example.

The eating monitoring device according to the present embodiment includes the detection device 2, and an information device 10 provided so as to be communicable with the detection device 2. The information device 10 is configured to execute the eating monitoring method according to the present embodiment. The information device 10 is, for example, a mobile device (smartphone, mobile computer, smart watch, mobile phone, etc.) or a personal computer.

The detection device 2 includes the sensor unit 3 provided to continuously detect the movement of the jaw. The sensor unit 3 is, for example, an optical sensor such as a reflective photo interrupter (reflective photosensor), an infrared sensor, or an image sensor, or a microwave sensor. The sensor unit 3 may be a contact sensor provided with an acceleration sensor. The detection device 2 provided with a reflective photo interrupter as the sensor unit 3 will be described herein.

The detection device 2 may be an ear-worn device. The present embodiment will be described using an ear-worn device as the detection device 2. The detection device 2 can be formed into an L shape having a hook part 15 on one end and the sensor unit 3 on the other end. The detection device 2 can be placed behind the ear by hanging the hook part 15 on the upper part of the base of the auricle, and thus, the movement of a skin 20 on the surface of the mandible can be detected by the sensor unit 3. For example, the detection device 2 shown in FIG. 1 can be worn on the ear as shown in FIG. 2.

A battery 16 of the detection device 2 can be placed in a corner of the L shape. The battery 16 may be a primary battery or a secondary battery (rechargeable battery).

The sensor unit 3 has a light emitting unit 4 and a photoelectric conversion unit 5.

During detection of the movement of the jaw by the sensor unit 3, the light emitting unit 3 emits light toward the skin 20 as shown in FIG. 3A. The emitted light passes through the skin 20, scatters in the skin 20, or is reflected by the skin 20. A portion of light reflected by the skin 20 enters the photoelectric conversion unit 5 and is photoelectrically converted, whereby a photocurrent is generated. As the wearer chews or opens or closes his/her mouth, the movement of the skin 20 changes from the state shown in FIG. 3A to the state shown in FIG. 3B, and distances $D_1$ and $D_2$ between the skin 20 and both the light emitting unit 4 and the photoelectric conversion unit 5 vary. Further, the incidence angle of light on the skin 20 varies. Therefore, transmission, scattering, and reflection of light in the skin 20 vary. As a result, a quantity of light incident on the photoelectric conversion unit 5 varies, so that the magnitude of the photocurrent generated by the photoelectric conversion unit 5 varies. The magnitude of the photocurrent generated by the photoelectric conversion unit 5 varies depending on the magnitude of the movement of the skin 20 due to chewing of the wearer wearing the detection device 2, the shape of the face of the wearer wearing the detection device 2, etc., and therefore, the magnitude and variation of the photocurrent generated by the photoelectric conversion unit 5 are different with each person.

For example, when the movement of the skin 20 due to chewing is detected by the detection device 2, the distance D between the skin 20 and both the light emitting unit 4 and the photoelectric conversion unit 5 periodically varies like $D_1 \rightarrow D_2 \rightarrow D_1 \rightarrow D_2 \rightarrow D_1 \rightarrow_2$. The incidence angle of light on the skin 20 also periodically varies. Therefore, the magnitude of the photocurrent generated by the photoelectric conversion unit 5 due to chewing also periodically varies, so that the sensor output of the sensor unit 3 also periodically varies.

The sensor unit 3 continuously outputs the magnitude of the photocurrent generated by the photoelectric conversion unit 5 as a sensor output. The sensor output may be a signal obtained by amplifying the photocurrent. The sensor output value of the sensor unit 3 is continuously transmitted from a communication unit 7a, and received by a communication unit 7c of the information device 10. Then, the sensor output value is stored in a storage unit 11 of a control unit 6b of the information device 10. The sensor output value may be amplified by the control unit 6b and subjected to a filtering process to be converted into a measured value. The filtering process may be performed using, for example, a low-pass filter, a high-pass filter, or a band-pass filter.

The communication system of the communication units 7a and 7c is, for example, a wired LAN system, a wireless LAN system, Bluetooth (registered trademark), ZigBee (registered trademark), or LPWA.

The control unit 6b may be composed of a CPU, a RAM, a storage, and the like.

Figure 5:
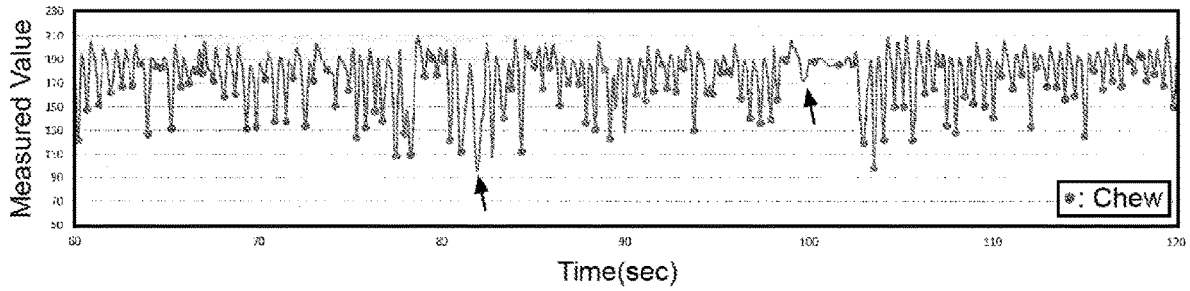
FIG. 5 is a graph showing a variation in a measured value of the sensor unit during a meal.

Since the sensor output of the sensor unit 3 due to chewing periodically varies, the temporal variation in the measured value of the sensor unit 3 is represented by an oscillation curve that vertically oscillates with chewing. For example, the temporal variation in the measured value of the sensor unit 3 due to chewing is as shown in FIG. 5.

The control unit 6b judges whether chewing is performed using a chewing judgment algorithm on the basis of the temporal variation in the measured value of the sensor unit 3 during a meal, and calculates the number of chews or the like. The chewing judgment algorithm is an algorithm for judging whether the variation in the measured value is caused by chewing.

As described above, the magnitude of the photocurrent generated by the photoelectric conversion unit 5 due to chewing periodically varies. Therefore, the measured value also periodically varies due to chewing. However, the mandible also moves when the wearer speaks, produces a sound, yawns, sneezes, coughs, and opens his/her mouth, for example, by which the measured value of the sensor unit 3 vertically oscillates. For this reason, in order to measure the number of chews, it is necessary to judge whether the vertical oscillation of the measured value of the sensor unit 3 is caused by chewing. The chewing judgment algorithm is used for such judgment.

Figure 6:
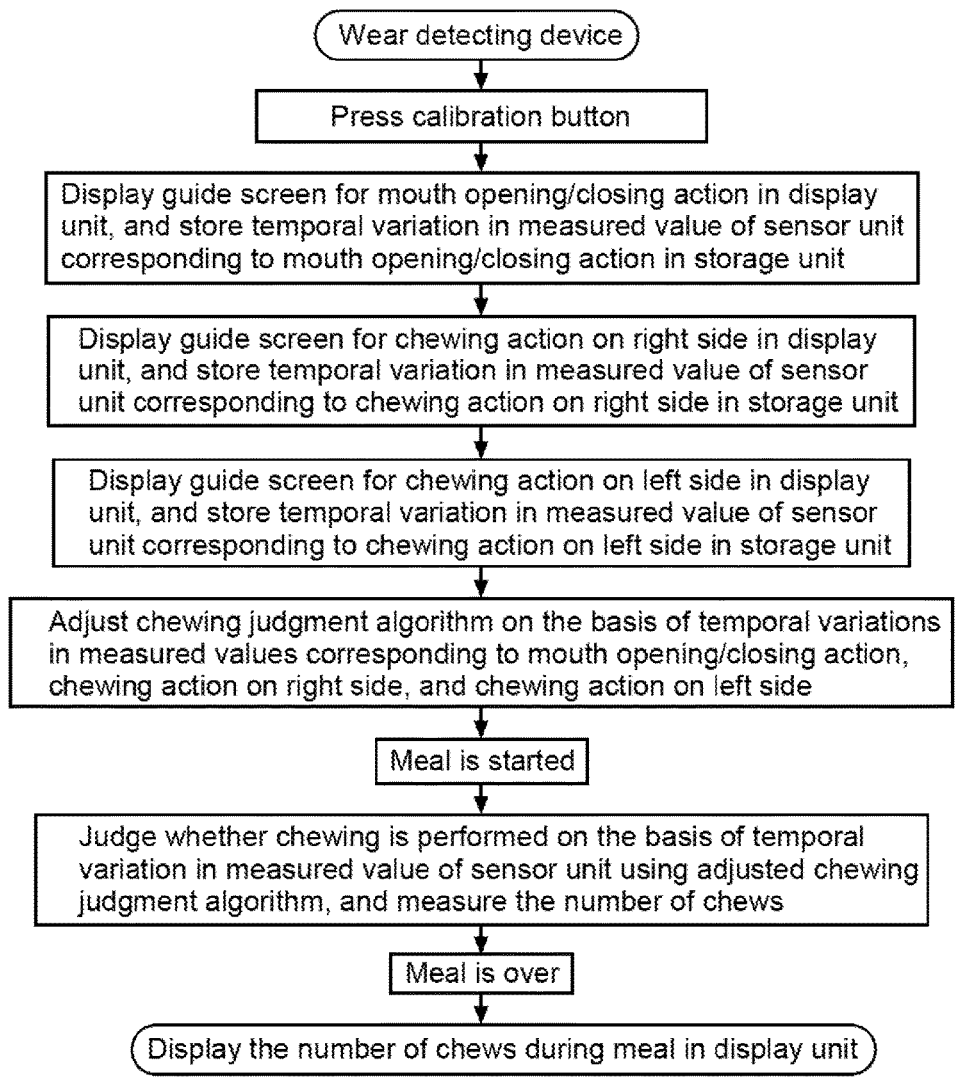
FIG. 6 is a flowchart of an eating monitoring method according to one embodiment of the present invention.

In the eating monitoring method according to the present embodiment, the chewing judgment algorithm is adjusted by calibration, it is judged whether chewing is performed on the basis of the temporal variation in the measured value using the adjusted chewing judgment algorithm, and the number of chews is measured. A standard chewing judgment algorithm is stored in the storage unit 11 of the control unit 6b. The control unit 6b adjusts the chewing judgment algorithm, and creates the adjusted chewing judgment algorithm. The calibration may be performed per meal, or may be performed periodically (for example, once a month). FIG. 6 is a flowchart showing the eating monitoring method according to the present embodiment.

First, a user presses a switch 18 to activate the detection device 2, and wears the detection device 2 on his/her ear. When the detection device 2 is activated, a signal is transmitted to the information device 10 from the communication unit 7a, whereby an eating monitoring application is started in the information device 10, and an eating monitoring screen is displayed in a display unit 12.

Figure 7A:
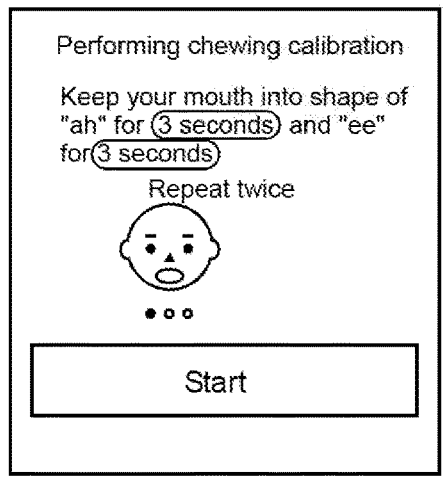
FIGS. 7A to 7F are views of a guide screen displayed in a display unit during calibration.

Next, the user presses a calibration button displayed in the display unit 12 to start calibration. When the calibration is started, a guide screen for a mouth opening/closing action is firstly displayed in the display unit 12. For example, a guide screen as shown in FIG. 7A is displayed. In this guide screen, a face in which a mouth is shaped into "ah" is displayed, and three count-up lamps are displayed below the face. The three lamps are lighted one by one per second from the left. During this three-second period, the guide screen prompts the user to shape his/her mouth into "ah".

Figure 7B:
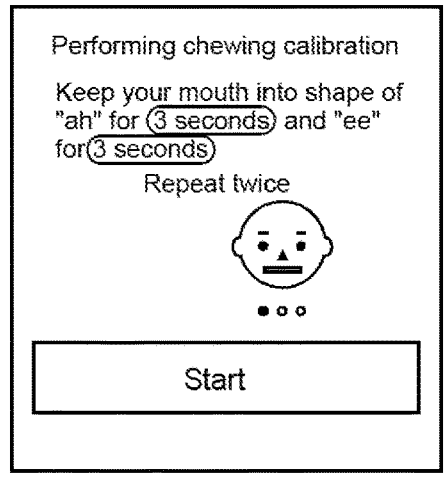

Then, the screen is switched to a guide screen as shown in FIG. 7B. In this guide screen, a face in which a mouth is shaped into "ee" is displayed, and three count-up lamps are displayed below the face. The three lamps are lighted one by one per second from the left. During this three-second period, the guide screen prompts the user to shape his/her mouth into "ee". The guide for the mouth of "ah" and the guide for the mouth of "ee" are repeated twice.

A message "Keep your mouth into shape of "ah" for 3 seconds and "ee" for 3 seconds. Repeat twice" is displayed as character information as shown in FIGS. 7A and 7B. The word "3 seconds" is enclosed by a line so as to be highlighted. The word may be highlighted by changing a color or font.

As shown in FIG. 7A, the face with the mouth of "ah" is displayed on the left side of the screen, and the face with the mouth of "ee" is displayed on the right side of the screen. This makes the user easily recognize switching between the mouth of "ah" and the mouth of "ee".

Figure 8:
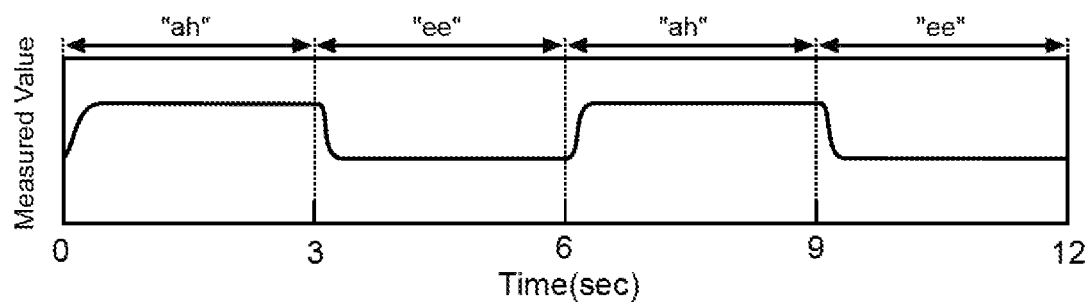
FIG. 8 is an explanatory view of a variation in a measured value corresponding to a mouth opening/closing action.

When the user wearing the detection device 2 repeats to shape the mouth into "ah" and "ee" in accordance with the guide screen, the measured value calculated from the sensor output of the sensor unit 3 varies as shown in FIG. 8, for example. In this case, when the user has the mouth of "ah", the measured value increases, and when the user has the mouth of "ee", the measured value decreases. It is found that, while chewing, the measured value increases when the upper teeth and the lower teeth of the user are separated from each other, and the measured value decreases when the upper teeth and the lower teeth contact. In this case, the chewing judgment algorithm is adjusted such that chewing is counted at the bottoms of the oscillation curve representing the measured value corresponding to the chewing during a meal. When the adjusted chewing judgment algorithm is used, chewing is counted at each black circle in the graph shown in FIG. 5, for example.

The chewing judgment algorithm can be adjusted at the end of the calibration.

When another user wears the detection device 2, and repeats to shape the mouth into "ah" and "ee", the measured value may decrease when the user shapes the mouth into "ah", and the measured value may increase when the user shapes the mouth into "ee". In this case, while chewing, the measured value decreases when the upper teeth and the lower teeth of the user are separated from each other, and the measured value increases when the upper teeth and the lower teeth of the user contact. In this case, the chewing judgment algorithm is adjusted such that chewing is counted at the tops of the oscillation curve of the measured value corresponding to chewing during a meal.

Figure 7C:
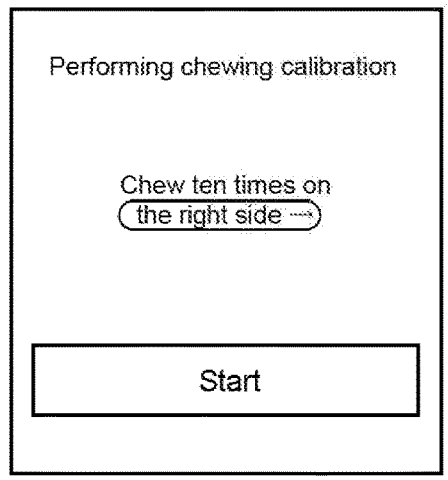

Next, a guide screen for a chewing action on the right side of the mouth is displayed in the display unit 12. For example, a guide screen as shown in FIG. 7C is displayed. A message "Chew ten times on the right side →" is displayed as character information as shown in FIG. 7C. The word "on the right side →" is enclosed with a line so as to be highlighted. The word may be highlighted by changing a color or font. The right arrow is displayed together, which makes the message easy to understand visually. The user is prompted to chew ten times on the right side by this guide screen.

Figure 7D:
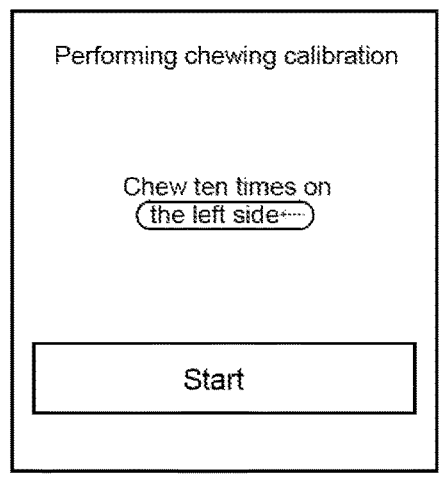

Then, a guide screen for a chewing action on the left side is displayed in the display unit 12. For example, a guide screen as shown in FIG. 7D is displayed. A message "Chew ten times on the left side ←" is displayed as character information as shown in FIG. 7D. The word "on the left side ←" is enclosed with a line so as to be highlighted. The word may be highlighted by changing a color or font. The left arrow is displayed together, which makes the message easy to understand visually. The user is prompted to chew ten times on the left side by this guide screen. The timing of occlusion is not designated in the guide screens described above.

The right side indicates the direction to the west when a person is facing south, and the left side indicates the direction to the east when a person is facing south.

Figure 9:
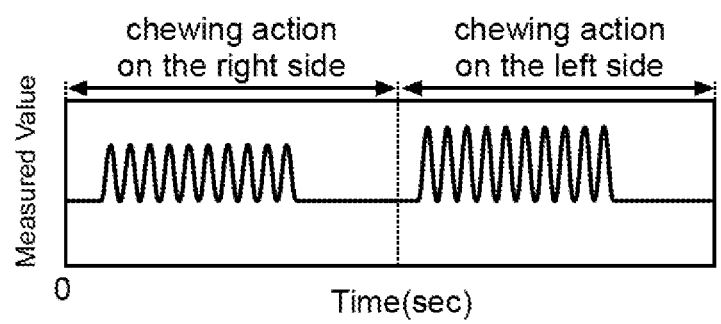
FIG. 9 is an explanatory view of a variation in a measured value corresponding to a chewing action.

When the user wearing the detection device 2 on the right ear chews ten times on the right side and chews ten times on the left side in accordance with the guide screen described above, the measured value calculated from the sensor output of the sensor unit 3 varies as shown in FIG. 9, for example. In this case, the oscillation of the measured value corresponding to the chewing action on the right side and the oscillation of the measured value corresponding to the chewing action on the left side are substantially the same in tempo, whereas the amplitude of the oscillation of the measured value corresponding to the chewing action on the left side is greater than the amplitude of the oscillation of the measured value corresponding to the chewing action on the right side. In this case, the chewing judgment algorithm is adjusted such that the oscillation having greater amplitude is counted as the chewing action on the left side, and the oscillation with smaller amplitude is counted as the chewing action on the right side. Thus, the chewing action on the right side and the chewing action on the left side can be accurately counted and distinguished using the feature amounts of the respective chewing actions, whereby the user can see the balance between the chewing action on the right side and the chewing action on the left side.

If the detection device 2 is worn on the left ear, the amplitude of the oscillation of the measured value corresponding to the chewing action on the right side is greater than the amplitude of the oscillation of the measured value corresponding to the chewing action on the left side. Therefore, the chewing judgment algorithm is adjusted such that the oscillation having greater amplitude is counted as the chewing action on the right side, and the oscillation with smaller amplitude is counted as the chewing action on the left side.

As described above, the amplitude of the measured value of the chewing action on the ear not wearing the detection device 2 (hereinafter referred to as a non-wearing-side chewing action) is greater than the amplitude of the measured value of the chewing action on the ear wearing the detection device 2 (hereinafter referred to as a wearing-side chewing action).

The calibration using the chewing action on the right side and the chewing action on the left side has been described above. However, if the calibration is performed with food being placed on both sides of the mouth, the chewing action on both sides and the chewing actions on the right and left sides can be accurately counted and distinguished on the basis of the feature amounts of the respective chewing actions.

In the present embodiment, the chewing actions on the left and right sides are used as calibration data, and the chewing action on the left side and the chewing action on the right side can be counted individually. Meanwhile, when various oral events are used as the calibration data, the period and proportion of the target event can be estimated. Examples of events for estimation target include a difference in type of food. That is, what kind of food the user actually eats can be estimated by learning chewing information when the user eats meat and chewing information when the user eats vegetables, and it is possible to prompt the user to modify the behavior by giving advice using the notification unit (display unit 12). Chewing actions differ depending on physical properties (water content, degree of adhesion, degree of viscosity, hardness, and coagulation) and amount of food, and an increase in the number of calibration information leads to accurate counting of the number of chews for various kinds of food and improvement of accuracy in estimating food.

When acts of, for example, coughing, talking, swallowing, laughing, yawning, and nodding are used as calibration data, the period other than the chewing action can be estimated. Thus, it is possible to reduce erroneous detection of chewing by not performing the judgment of chewing during the abovementioned actions. Further, the notification unit may notify the user of the abovementioned actions for behavior modifications and various diagnoses.

The tempos of the oscillations of the measured values corresponding to the chewing action on the right side and the chewing action on the left side, and maximum values, minimum values, average values, and the like of the amplitudes are calculated. The chewing judgment algorithm is adjusted such that the oscillation greatly deviated from the oscillation pattern of the measured values corresponding to the chewing action on the right side and the chewing action on the left side is not counted as a chewing action on the basis of the calculated maximum values, minimum values, average values, and the like. This can prevent the acts of talking, producing a sound, yawning, sneezing, coughing, and opening the mouth from being counted as a chewing action, whereby the number of chews can be accurately counted. When the adjusted chewing judgment algorithm is used, the oscillations indicated by arrows in the oscillation curve in the graph shown in FIG. 5 are not counted as a chewing action, for example.

The calibration is thus ended in the present embodiment.

Due to the calibration described above, the chewing judgment algorithm adjusted for each user can be created, and whether chewing is performed can be judged with high accuracy. Accordingly, a variation in accuracy of judgment of chewing due to personal differences can be reduced.

Next, when the user presses a "meal start" button displayed in the display unit 12 of the information device 10 upon the start of a meal, whether chewing is performed is judged on the basis of the oscillation curve of the measured value using the adjusted chewing judgment algorithm, and the number of chews is counted.

During the meal, the number of chews on the right side, the number of chews on the left side, and the sum of the number of chews on the right side and the number of chews on the left side are counted and displayed in the display unit 12. This enables the user to find, for example, the number of chews per bite and the balance between the chewing action on the right side and the chewing action on the left side, and thus, the user takes a meal while being conscious of chewing. This may lead to behavior modifications.

When the meal is over, the user presses a "meal over" button displayed in the display unit 12 of the information device 10. When this button is pressed, the number of chews on the right side, the number of chews on the left side, and the sum of the number of chews on the right side and the number of chews on the left side during the meal, a comparison with the previous meal, a score for a manner of eating, an advice for a manner of eating, etc. are displayed in the display unit 12.

Second Embodiment

Figure 10:
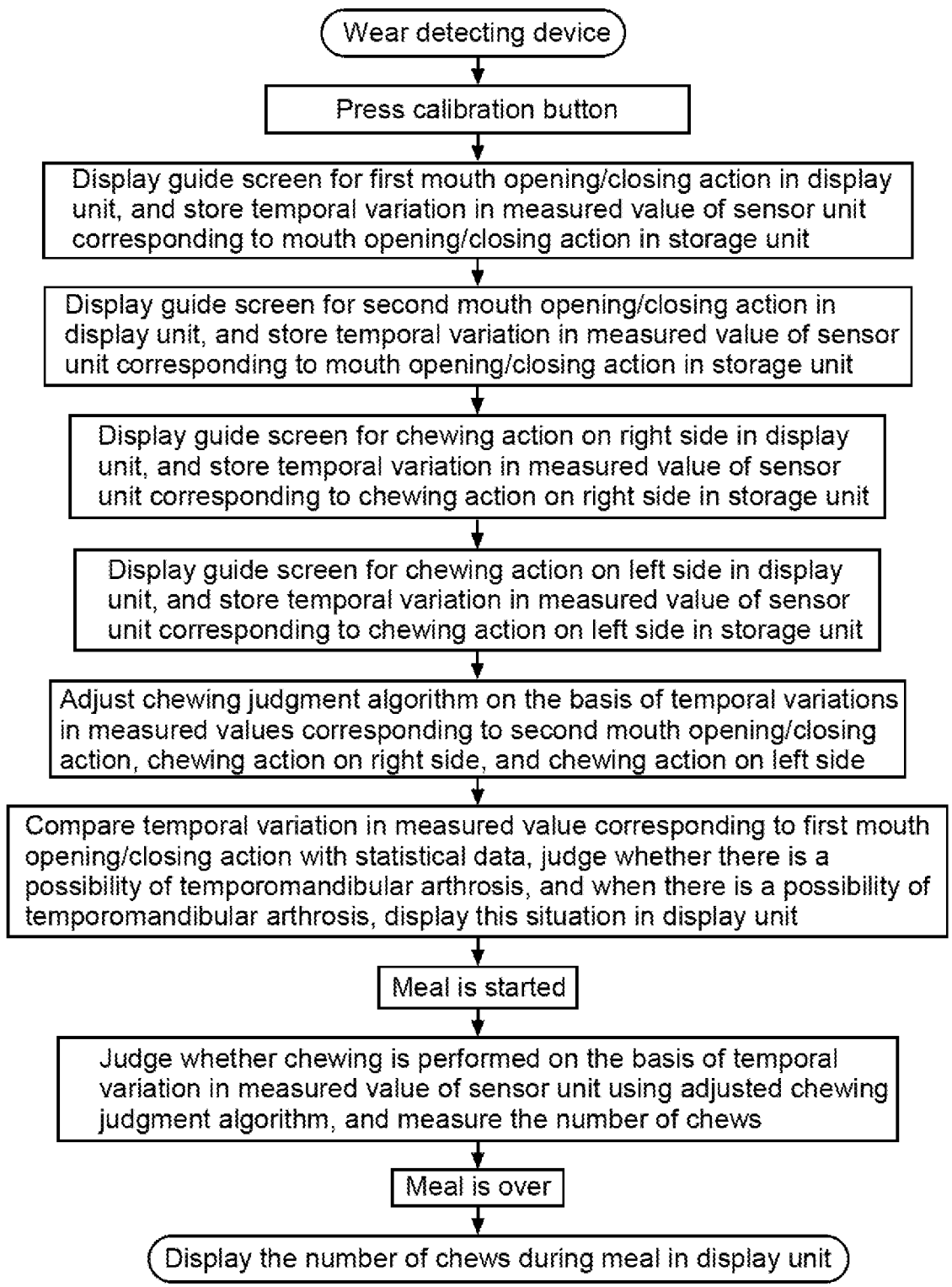
FIG. 10 is a flowchart of an eating monitoring method according to one embodiment of the present invention.

In the second embodiment, a guide screen for a first mouth opening/closing action for prompting the user to slowly open and close his/her mouth is displayed in the display unit 12 of the information device 10 during calibration. FIG. 10 is a flowchart of an eating monitoring method according to the second embodiment. In the second embodiment, the calibration for the mouth opening/closing action (second mouth opening/closing action), the chewing action on the right side, and the chewing action on the left side described in the first embodiment is also performed in the same manner as in the first embodiment. Here, the calibration for the first mouth opening/closing action and matters related thereto will be described.

Figure 7E:
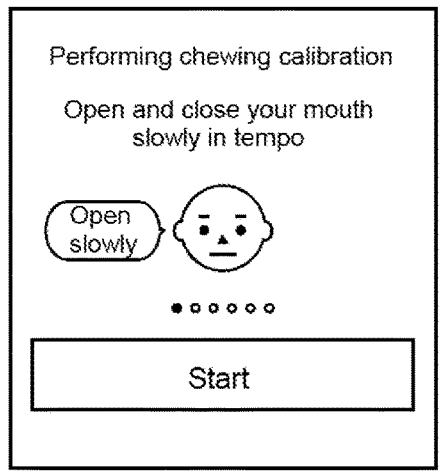

A guide screen for the first mouth opening/closing action is displayed in the display unit 12. For example, a guide screen as shown in FIG. 7E is displayed. In this guide screen, a face is displayed, and six count-up lamps are displayed below the face. The count-up lamps are lighted one by one per second from the left. A message "Open and close your mouth slowly in tempo" is also displayed as character information. In the first three seconds counted by the count-up lamps, a message "Open slowly" is displayed in a balloon beside the face in the display unit 12, and the mouth in the face displayed in the display unit 12 slowly opens. In the remaining three seconds counted by the count-up lamps, a message "Close slowly" is displayed in the balloon beside the face in the display unit 12, and the mouth in the face displayed in the display unit 12 slowly closes.

Regarding the display showing that the mouth opens slowly, the mouth may open smoothly, or the shape of the mouth may be switched in a stepwise manner in accordance with lighting of the count-up lamps, in the first three seconds. Regarding the display showing that the mouth closes slowly, the mouth may close smoothly, or the shape of the mouth may be switched in a stepwise manner in accordance with lighting of the count-up lamps, in the remaining three seconds.

When the user wearing the detection device 2 slowly opens and closes his/her mouth in accordance with the guide screen described above, the curve indicating the temporal variation in the measured value calculated from the sensor output of the sensor unit 3 has a waveform according to the user's manner of opening and closing the mouth. For example, when the mouth is smoothly opened and closed, the curve indicating the temporal variation in the measured value has a waveform that smoothly oscillates vertically, and when the mouth is not smoothly opened and closed, the curve indicating the temporal variation in the measured value does not have a waveform that smoothly oscillates vertically. Particularly when the user has temporomandibular arthrosis, the curve indicating the temporal variation in the measured value has a unique waveform.

Next, the waveform of the curve indicating the temporal variation in the measured value corresponding to the first mouth opening/closing action is compared with statistical data. The statistical data indicates a tendency of a waveform of a curve indicating a temporal variation in a measured value corresponding to the first mouth opening/closing action of a person having temporomandibular arthrosis. It can be judged whether the user may have temporomandibular arthrosis through the comparison with the statistical data described above. If it is judged that the user may have temporomandibular arthrosis as a result of the judgment, the display unit 12 of the information device 10 displays that the user may have temporomandibular arthrosis. Thus, a possibility of temporomandibular arthrosis can be found.

The statistical data may be stored in the storage unit 11 of the information device 10, or the information device 10 may download the statistical data from a server 13 via the communication unit 7b. Further, the waveform of the curve indicating the temporal variation in the measure value measured during calibration may be uploaded to the server 13, and compared to the statistical data in the server 13.

In addition, the waveform of the curve indicating the temporal variation in the measured value and the statistical data may be compared in the server 13 using artificial intelligence. This makes it possible to detect a possibility of diseases other than temporomandibular arthrosis.

The other configurations are the same as those in the first embodiment. The description of the first embodiment is applicable to the second embodiment, unless there is anything inconsistent.

Third Embodiment

Figure 11:
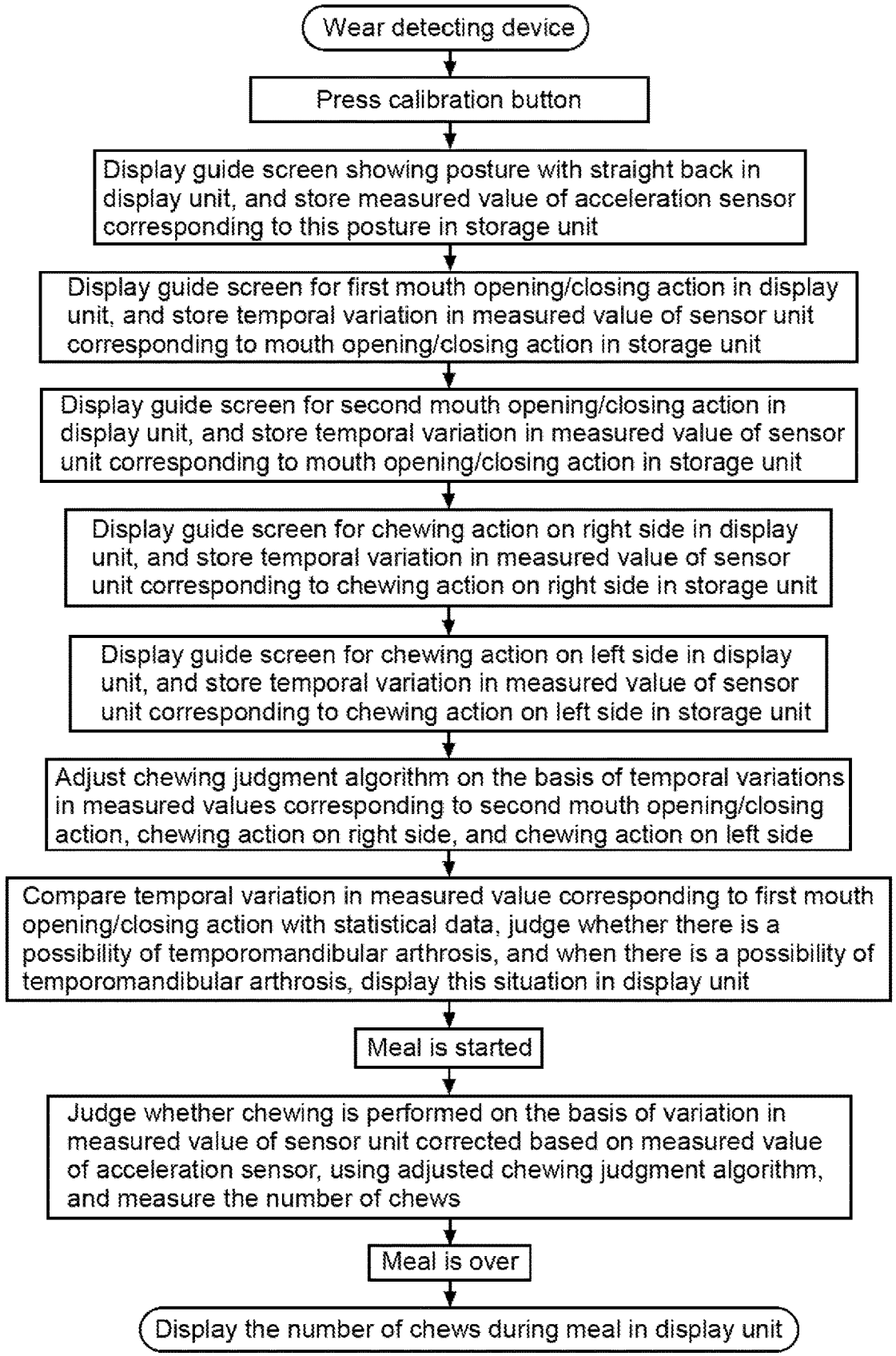
FIG. 11 is a flowchart of an eating monitoring method according to one embodiment of the present invention.

In the third embodiment, a guide screen for prompting the user wearing the detection device 2 to keep his/her back straight is displayed in the display unit 12 of the information device 10 during calibration. FIG. 11 is a flowchart of an eating monitoring method according to the third embodiment. In the third embodiment, the calibration for the mouth opening/closing action (second mouth opening/closing action), the first mouth opening/closing action, the chewing action on the right side, and the chewing action on the left side described in the first and second embodiments is also performed in the same manner as in the second embodiment. Here, the calibration in which the user is prompted to keep his/her back straight and matters related thereto will be described.

In the third embodiment, the detection device 2 is provided with an acceleration sensor 8. The detection device 2 can be configured to include a 3-axis acceleration sensor.

The acceleration sensor 8 continuously outputs a sensor output. The sensor output value is continuously transmitted from the communication unit 7a, and received by the communication unit 7c of the information device 10. Then, the sensor output value is stored in the storage unit 11 of the control unit 6b of the information device 10. The sensor output value may be amplified by the control unit 6b, and subjected to a filtering process so as to be converted into a measured value. The filtering process may be performed using, for example, a low-pass filter, a high-pass filter, or a band-pass filter.

When the measured value of the acceleration sensor 8 is analyzed by the control unit 6b, the horizontal state of the detection device 2, the direction of gravity, and the like can be detected, whereby the posture of the user wearing the detection device 2 can be detected.

Figure 7F:
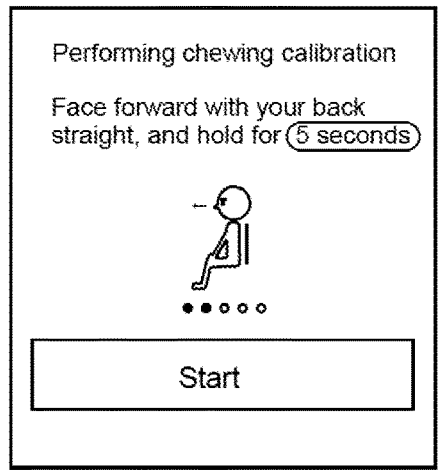

During calibration, a guide screen for prompting the user to keep his/her back straight is displayed in the display unit 12 of the information device 10. For example, a guide screen as shown in FIG. 7F is displayed. In this guide screen, a person with straight back and an arrow indicating gaze are displayed, and five count-up lamps are displayed below the person. The lamps are lighted one by one per second from the left. A message "Face forward with back straight, and hold for 5 seconds" is also displayed as character information. The word "5 seconds" is enclosed by a line so as to be highlighted. The word may be highlighted by changing a color or font.

When the user wearing the detection device 2 keeps his/her straight back and hold for five seconds in accordance with the guide screen described above, the measured value of the acceleration sensor 8 is stabilized. The direction of gravity detected through analysis of the stabilized measured value corresponds to the direction of gravity corresponding to the state of the user who holds with his/her back straight. The control unit 6b adjusts a posture judgment algorithm such that the direction of gravity is used as a reference direction. A standard posture judgment algorithm is stored in the storage unit 11, and the control unit 6b adjusts the posture judgment algorithm to create an adjusted posture judgment algorithm.

The posture of the user during a meal is judged on the basis of the measured value of the acceleration sensor 8 using the adjusted posture judgment algorithm.

For example, when the user bends his/her back, looks down, or leans his/her head during a meal, the direction of gravity detected from the measured value of the acceleration sensor 8 varies. Therefore, the posture of the user can be judged by comparing the direction of gravity detected from the measured value of the acceleration sensor 8 using the adjusted posture judgment algorithm with the reference direction.

When the posture of the user changes during a meal, the brightness of the skin 20, the movement of the skin 20, the position where the detection device 2 is worn, and the like vary, so that the measured value of the sensor unit 3 may vary.

In the present embodiment, the measured value of the sensor unit 3 is corrected or the chewing judgment algorithm is corrected on the basis of the posture of the user detected using the posture judgment algorithm. Thus, the accuracy in the judgment of chewing using the adjusted chewing judgment algorithm can be improved.

When it is detected with the acceleration sensor 8 that the user has a bad posture during a meal, the display unit 12 may show that the user has a bad posture. For example, a message such as "Your back is bent", "You are leaning to the right", or "You are leaning to the left" may be displayed in the display unit 12. This enables the user to objectively recognize his/her posture.

The other configurations are the same as those in the first or second embodiment. The description of the first or second embodiment is applicable to the third embodiment, unless there is anything inconsistent.

Fourth Embodiment

In the first to third embodiments, data processing is performed in the information device 10. In the fourth embodiment, the detection device 2 includes a control unit 6a, and the control unit 6a performs data processing. In the first to third embodiments, the guide screen is displayed in the display unit 12 of the information device 10 for assisting the movement of the user. On the other hand, in the fourth embodiment, the detection device 2 has a speaker 22, and the speaker 22 assists the movement of the user by sound.

In the fourth embodiment, the detection device 2 serves as the eating monitoring device 8.

The control unit 6a provided to the detection device 2 may include a microcontroller having a CPU, a memory (storage unit), a timer, and an input/output port, for example. The storage unit included in the control unit 6a can be configured to include a ROM such as mask ROM, EPROM, EEPROM, or flash memory, and a RAM such as FeRAM, SRAM, or DRAM.

The other configurations are the same as those in the first to third embodiments. Further, the description regarding the control unit 6b of the information device 10 in the first to third embodiments is applicable to the fourth embodiment by replacing the control unit 6b with the control unit 6a. Moreover, the description regarding the display unit 12 of the information device 10 in the first to third embodiments is applicable to the fourth embodiment by replacing the function of the display unit 12 with the function of the speaker 22 of the detection device 2.

While the embodiments of the present invention have been described above, the scope of the present invention is not limited thereto, and various modifications are possible without departing from the spirit of the present invention. In addition, some or all of the embodiments of the present invention may be combined.

What is claimed is:

1. An eating monitoring method for judging whether a chewing action is performed or not by a chewing judgment algorithm on a basis of a temporal variation in a measured value of a reflective photo interrupter facing a skin of a person so as to detect a movement of a jaw of the person while the person takes a meal,
   the person wearing a detection device comprising the reflective photo interrupter, and using an information device comprising a port for communicating with the detection device,
   the method comprising:
   providing a visual guide or a voice guide to have the person to move the jaw;
   obtaining calibration data based on the measured value during the providing of the visual guide or the voice guide;
   adjusting the chewing judgment algorithm on the basis of the calibration data;
   and judging whether the chewing action is performed or not by the chewing judgment algorithm which has been adjusted, and measuring a number of chews on the basis of the temporal variation in the measured value of the reflective photo interrupter during the meal.

2. The eating monitoring method according to claim 1, wherein
   in the adjusting the chewing judgment algorithm, the chewing judgment algorithm is adjusted for each of a chewing action on the right side and a chewing action on the left side of the person wearing the detection device.

3. The eating monitoring method according to claim 1, further comprising comparing the temporal variation in the measured value of the reflective photo interrupter with statistical data, the temporal variation corresponding to a mouth opening/closing action of the person wearing the detection device.

4. The eating monitoring method according to claim 1, wherein the detection device comprises an acceleration sensor, and the eating monitoring method further comprises:

adjusting a posture judgment algorithm on the basis of a measured value of the acceleration sensor, the measured value of the acceleration sensor corresponding to a posture of the person wearing the detection device;

and judging the posture of the person by the adjusted posture judgment algorithm during the meal on the basis of the measured value of the acceleration sensor.

5. An eating monitoring device comprising the detection device and the information device, wherein the information device is configured to execute the eating monitoring method according to claim 1.

6. The eating monitoring device according to claim 5, wherein the detection device is configured to provide the measured value during movement of the jaw.

7. The eating monitoring device according to claim 5, wherein the detection device is formed into an L shape having a hook part on one end of the detection device and the reflective photo interrupter on the other end of the detection device, and has a battery placed at a corner of the L shape.

8. The eating monitoring method according to claim 1, wherein the visual guide or the voice guide is provided so that the person moves the jaw in time with the visual guide or the voice guide.

9. The eating monitoring method according to claim 8, wherein:

the visual guide or the voice guide informs the person a first time period to maintain a mouth of the person so that upper teeth and lower teeth are separated from each other, and a second time period to maintain the mouth so that the upper teeth and the lower teeth contact, and the calibration data is obtained from the measured value during the first and second time periods.

10. The eating monitoring method according to claim 8, wherein:

the visual guide or the voice guide provides a first tempo for opening a mouth of the person, and a second tempo for closing the mouth, and the temporal variation of the measured value is obtained for drawing a curve during the opening and the closing.

11. The eating monitoring method according to claim 9, wherein the chewing judgement algorithm is adjusted so that the chewing action is counted, depend on the measured value, as a number of bottoms or as a number of peaks of an oscillation curve of the measured value.

12. The eating monitoring method according to claim 1, wherein the voice guide is provided by a speaker included in the detection device.

13. The eating monitoring method according to claim 1, wherein the visual guide is provided by a display connected to the information device.

14. The eating monitoring method according to claim 3, wherein the statistical data is data indicating a tendency of a symptom.

* * * * *